United States Patent [19]

Sneider

[11] 4,351,339
[45] Sep. 28, 1982

[54] TAMPON WITH A PROTECTIVE ACCORDION-STYLE COVER

[76] Inventor: Vincent R. Sneider, 3422 Hallcrest Dr., Atlanta, Ga. 30319

[21] Appl. No.: 254,102

[22] Filed: Apr. 14, 1981

[51] Int. Cl.³ .............................................. A61F 13/20
[52] U.S. Cl. .................................................... 128/285
[58] Field of Search ....................... 128/263, 270, 285

[56] References Cited

U.S. PATENT DOCUMENTS

| | | | |
|---|---|---|---|
| 2,188,923 | 2/1940 | Robinson | 128/285 |
| 2,491,017 | 12/1949 | Robinson . | |
| 2,926,394 | 3/1960 | Bletzinger et al. | 128/285 |
| 2,926,667 | 3/1960 | Burger, Jr. et al. | 128/285 |
| 2,965,101 | 12/1960 | Schirmer et al. . | |
| 3,298,369 | 1/1967 | Pirie . | |

*Primary Examiner*—C. Fred Rosenbaum
*Attorney, Agent, or Firm*—Ralph R. Roberts

[57] ABSTRACT

A tampon assembly for use with and in body openings, said tampon having a close helically-wound absorbent member with the portions substantially parallel and contiguous to provide an outer support surface for a permeable cover that is pleated. The pleated cover has the folds overlaid so that in an inserting condition the pleats are disposed to retain their overlaid position during insertion. An inserting stick or rod is conventionally used for insertion. A withdrawal string is attached to the absorbent member at that end that faces the body opening. The cover at its withdrawal end captures the withdrawal string so that at the time of withdrawal the string is grasped and the cover and spiral wound absorbent member is manipulated from the opening causing at least a partial collapse of the absorbent member into a smaller diameter and with the string also withdrawing the pleated cover with the folds in said cover being unfolded to bring the cover into an unfolded condition and removal of the tampon assembly from the body opening is easily made with a reduction in diameter of the tampon.

7 Claims, 9 Drawing Figures

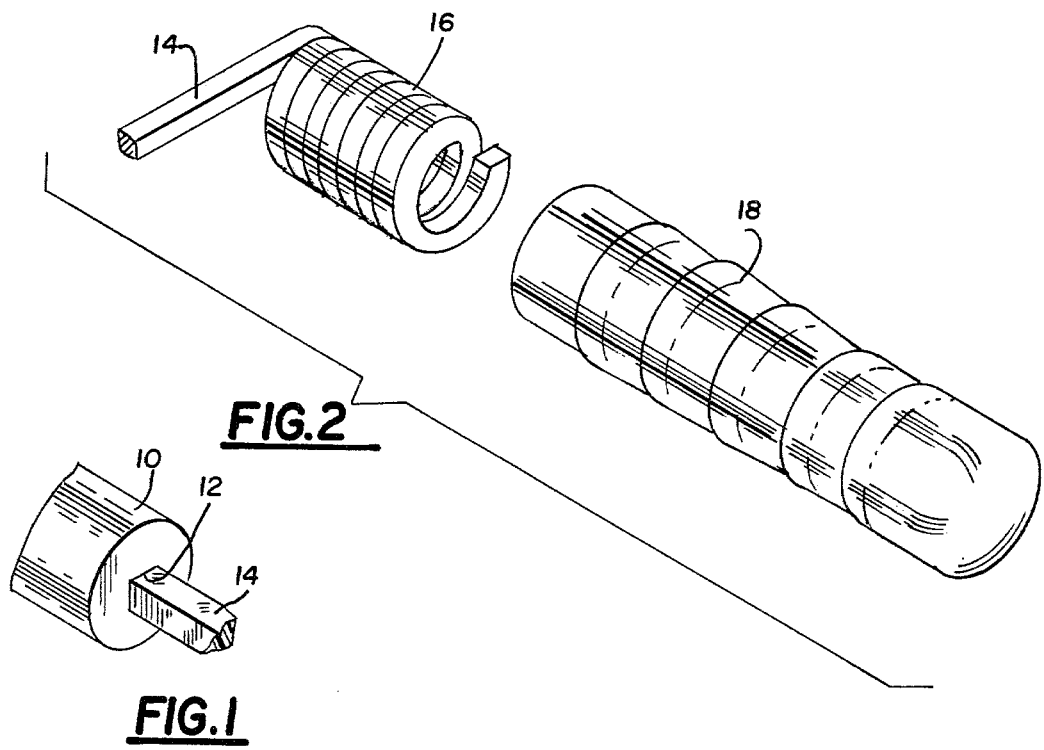
FIG. 2
FIG. 1
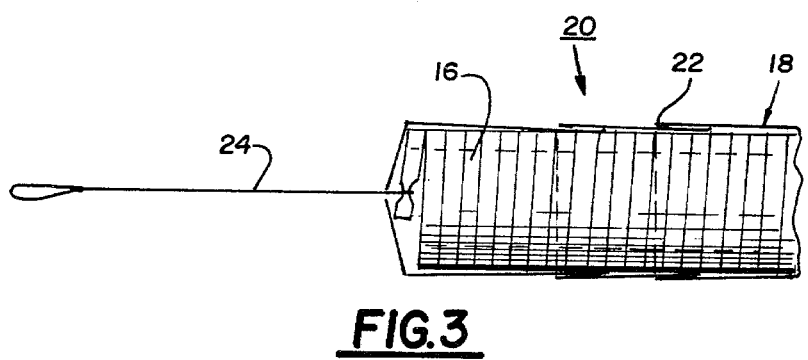
FIG. 3
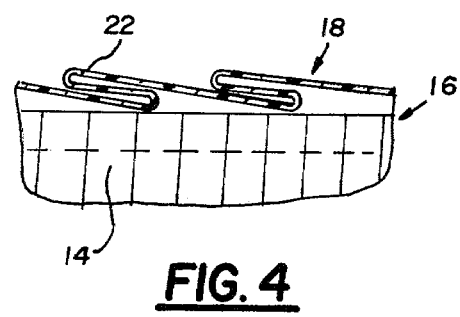
FIG. 4

TAMPON WITH A PROTECTIVE ACCORDION-STYLE COVER

BACKGROUND OF THE INVENTION

1. Field of the Invention

With reference to the classification of art as established in and by the U.S. Patent and Trademark Office this invention is believed to be found in the general class entitled, "Surgery" (Class 128) and in the subclass entitled, "Intravaginal" (Subclass 285). Also to be noted is subclass entitled "Tampon depositors" (Subclass 263) and subclass entitled, "Tampon" (Subclass 270).

2. Description of the Prior Art

Tampons having absorbent ability have been used for many years as a feminine hygiene assist. Variations, including the addition of medical components, have been used to provide medical treatment. Tampons in the medical field have been used for surgical dressings and also have included treatment for hemorrhoids and hemorrhoid operations. Tampons having increased absorbency may be used to alter or change normal reaction to medical treatment. These alterations or additions to regular tampons to include drugs and other medicants are not shown in the present invention. These additions are contemplated in the surgical construction of the absorbent material.

Tampons as presently used are objected to because of the discomfort during the withdrawal of the tampon itself. The insertion of the tampon is usually by a stick or similar device but after the tampon has been placed within the body cavity and particularly during catamenial use the absorbency of the tampon usually produces an uncomfortable feeling or irritation because of the dry state of the tampon against the vaginal wall. If used as a body healing surgical application the removal of this tampon often disturbs and irritates the healed or healing body tissues.

The inventor has made a careful pre-ex search and the results are noted in the PTO form 1449 and comments pertaining to those patents noted.

SUMMARY OF THE INVENTION

The present invention may be defined in part by reference to its objects. It is an object of this invention to provide, and it does provide, a helically wound tampon with an accordion-pleated outer covering. The conventional string is used so that after the desired absorbancy use the tampon may be and is withdrawn. In this invention the pleated covering and the helically wound tampon body is drawn to a degree sufficient so that with and by the withdrawal action the helical body and the covering sheath are reduced in diameter to permit easy withdrawal.

It is another object of this invention to provide, and it does provide, a tampon with an accordion-pleated covering which provides ready insertion by a stick or similar applicator. The absorbancy is provided by a helically wound member. Withdrawal of said member is by a string attached at one end. The permeable accordion-pleated covering and the helically wound absorbant member as it is withdrawn assumes a much smaller diameter than the initial inserting configuration.

This tampon has a body made of absorbent material which is extruded in a square or rectangular form after which it is wound into a tight helical configuration. One end of this helical winding is attached to a withdrawal string and this body portion of said tampon is covered by a permeable sheath having an accordion-pleated construction arranged so that at the time of insertion into the human body opening the outer covering is not disturbed. When tampon withdrawal is to be made the pulling of the string causes the accordion-pleated outer sheath or covering to lengthen and the helically wound member to uncoil and to allow withdrawal to be made at a reduced diameter. The winding is made of natural or synthetic material usually with a high absorbancy rate. This absorbant material is shaped into a closely wound or helical spiral with one end of the absorbant member attached to said string. The outer sheath or covering has a high permeability capacity and is formed as an overlaid accordion-pleated covering with or without an additional coating such as a petroleum jelly derivative as an assist for insertion of the tampon. At the time of withdrawal the string is grasped and pulled so that the outer sheath or covering is extended to its unfolded condition and an unwinding of the helically wound tampon body occurs and the extension provides a reduced diameter assembly that provides easy and comfortable withdrawal of the tampon from the human body opening.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen a specific embodiment of a tampon and the novel construction of said tampon as adopted for use in human body openings and showing a preferred means for construction and use. This specific embodiment has been chosen for the purposes of illustration and description as shown in the accompanying drawings wherein:

BRIEF DESCRIPTION OF THE DRAWINGS

FIG. 1 represents a more-or-less diagrammatic and isometric view representative of a die or head end of an extruder with the absorbent product extruded, this product is shown as a square configuration with an indefinite length of material;

FIG. 2 represents a diagrammatic, partly exploded isometric view of the absorbent material of FIG. 1 wound into a closely wound helical spiral with contiguous coils and ready for insertion and mounting in an outer cover;

FIG. 3 represents a diagrammatic side view of the assembled tampon with the fore end not shown, and depicting a preferred construction of the tampon;

FIG. 4 represents in a greatly enlarged scale a fragmentary side view and showing the accordion-pleated outer cover enclosing the contiguous helical wound body material;

Figure 6:
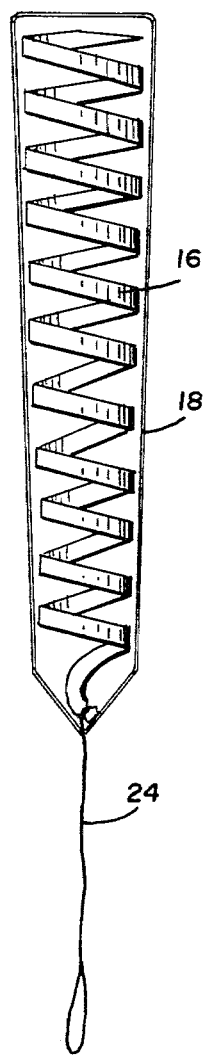
FIG. 6 represents an expanded and partially diagrammatic side view in enlarged scale and showing the used tampon being withdrawn.

In the following description and in the claims various details are identified by specific names for convenience. These names are intended to be generic in their applica-

EMBODIMENT OF FIG. 1

Referring next to the drawings and in particular to FIG. 1, it is to be noted that an extrusion die 10 for and as a part of an extruder, not shown, has at this discharge end an exit opening 12. From this exit opening body material 14 is shown being extruded. As depicted, the material is square or nearly so but in FIGS. 7B and 7C other configurations are suggested. This body material may be a natural fiber or may be synthetic or combinations thereof as long as it has the desired absorbent properties. It is anticipated that this material may be extruded into a tight helical spiral or may be formed or cut from sheet material then closely wound. The desired configuration of the body material may be square, rectangular or an other shape but when formed into a body the side-by-side coils are substantially arranged as contiguous and continuous on its outer or exterior diameter and surface. Whatever the composition of material it is anticipated that a high absorbency capability with or without added materials such as medicaments will provide a tampon having the desired properties.

EMBODIMENT OF FIG. 2

The tampon as shown in FIG. 2 is an isometric view in an expanded and diagrammatic representation and showing the body material 14 being wound or otherwise conformed into a tight, contiguous hollow body generally indicated as 16. This helically would body material is conformed so as to provide a substantially smooth and continuous outer surface which is covered by a pleated cover or sheath 18. This sheath or covering has an ability to pass fluids through the walls thereof. The ability to pass fluids through said covering is in accordance with the contemplated use of the tampon. Not shown but anticipated is that the covering or sheath 18 may have a small affinity to the helically wound body material 14 so that this covering is retained in the body opening in its inserted condition.

TAMPON ASSEMBLY OF FIG. 3

In FIG. 3 is shown the assembled tampon identified generally as 20. As shown in a diagrammatic side view the inserting end is not shown and the tampon is also depicted in an enlarged scale. The helically wound body assembly 16 is shown closely wound with the absorbent members adjacent each other and providing a smooth outer surface. The pleated outer sheath 18 is shown with accordion pleats 22 so that the applied cover smoothly and snugly encloses and retains the absorbent body 16. The accordion-pleats 22 are shown with the fold portions disposed so that the inner folds are toward the inner body member 16. A withdrawal string 24 is attached as by tying to one end of a coil of the inner absorbent body member 14. This outer cover or sheath 18 is closed at the inserting end and the withdrawal end is made with a small opening around said string or may be directly attached to the withdrawal string. At the time of withdrawal the string 24 will move or engage the body material 14 to assist in removal.

SHEATH CONFIGURATION AS IN FIG. 4

In FIG. 4 there is shown a fragmentary and partly diagrammatic depiction of the preferred configuration of the pleated sheath or cover 18. As shown the absorbent material 14 is arranged to provide a helical support or body 16 for the outer cover which is pleated to provide accordion-pleats 22. These pleats are overlaid so that when withdrawal of the tampon is to be made the pleats will unfold to lengthen into a much longer confining means. It is to be noted that accordion-type pleats are shown as providing the easiest to make but other pleated construction may be provided since the tampon as an assembly is normally carried within an inserting tube of plastic or paper. This tube is usually discarded after insertion.

EMBODIMENT OF FIG. 5

Figure 5:
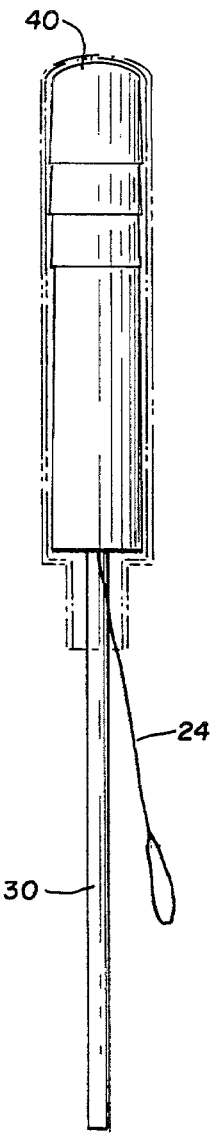
FIG. 5 represents a side view of the tampon assembly and an associated stick and ready for insertion into a body opening.

FIG. 5 represents a side view of the tampon 20 with the inserting, throw-away tube 40 (phantom outline) enclosing the pleated cover 18. The tube may be provided with a lubricant for an assist during insertion. After insertion in the usual manner into the body opening the stick 30 and the tube are discarded. The tube and stick 30 are conventional and no patentable distinction is ascribed thereto. Said tube may have a reduced diameter grasping end through which the stick 30 extends so as to provide one-hand manipulation. The stick may be wood, plastic or some combination thereof and the selection is merely a matter of use and preference.

EMBODIMENT OF FIG. 6

The withdrawal of the tampon 20 is depicted in FIG. 6 and the particular construction which provides the comfortable removal of this tampon. The withdrawal string 24 is grasped and in and by a withdrawal action and motion the tampon assembly is moved toward the body opening. Movement of the string 24 causes the cover 18 and spirally wound body portion 16 to uncoil and assume a much smaller diameter. This reduction is achieved when the string 24 engages the tied end of the last spiral winding of the body 16. Usually the absorbent body member is damp and at least partially limp. As and during withdrawal the outer cover 18 is extended and the pleats disappear and with the spiral body is reduced in diameter. The outer cover 18 conforms to the partially collapsed body. The withdrawal action causes the absorbent body member 16 and the cover 18 to assume the smaller diameter with the unwinding of the spiral and the lengthening of the cover allowing easy withdrawal of the tampon.

EMBODIMENTS OF FIGS. 7A, 7B AND 7C

Figures 7A, 7B, 7C:
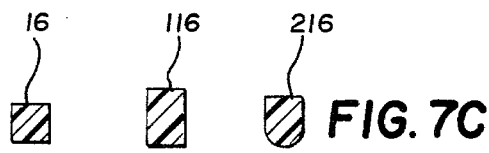
FIGS. 7A, 7B and 7C represent sectional views of the shapes in which absorbent material may be formed or extruded.

It is to be noted that the extruded material as shown in FIGS. 1 and 2 has a more-or-less square configuration. In FIG. 7A this extrusion is shown with substantially sharp corners but this same configuration may have slightly rounded corners. Whether as an extrusion or as a member cut from a sheet-like supply it is contemplated that the body member 16 be conformed into a helical spiral winding. FIG. 7B is shown as a rectangular shape and when the body is formed the narrow or wide side may be arranged to provide the outside surface. This body member 116, as an extrusion, may have a small radius at the corners to utilize an extrusion die within the practical limits of forming the extrusion. The formation of the corners or the radiusing of the corners of course depends of the composition of the material being extruded. As a strip cut from a sheet the corners are normally sharp.

In FIG. 7C the body member is identified as 216 and is shown with an inner portion that is curved into a more-or-less arcuate configuration. The inner curved portion 40 may be any selected shape as long as the outer portion is substantially flat when the body member 216 is wound into a tight and contiguous assembly. It is desirable that the outer surface be substantially flat when the body is formed and the side extents be substantially parallel.

Whatever the composition of material such as all natural fiber, all synthetic material or mixtures thereof, the composition of the body material will provide the desired absorbency rate or capability. The outer covering of the tampon may be natural, synthetic or mixtures thereof and may be completely porous or only partially porous depending upon the use of the tampon. Whether a medicament is used with the body or cover will depend on the use of the tampon. Lubricant to the tip or cover is a matter of preference and use and may be provided at the time of manufacture or at the time of use. Lubrication is not a novel concept but what is novel is the use of pleats in the cover and the tight helical winding of the body to provide spirals that may be unwound at the time of withdrawal causing the body and cover to be reduced in diameter to achieve an easy withdrawal.

The tampon shown and described in connection with the drawings is substantially conventional in use and application. The insertion and use is like that usually provided and with or without medicament treatment is readily used by women or others when particular problems are to be treated. The withdrawal string 24 may be a cord or tape and the securing to a cover or securing with a very small hole in said cover is merely a matter of selection. The stick 30 may have its length made more-or-less than shown and the use of plastic tubes for stick members is well known and also is a matter of choice. Pleats in the outer cover are preferably of the accordion-type but may be other types and in FIG. 5 are only suggested in the representation. The pleats are as close and as numerous as desired. In the withdrawal action these pleats disappear and the outer sheath or cover becomes a smaller and flexible tube-like member that encloses but does not restrict the absorbent body 16. The tampon above described has mentioned human beings but, of course, may have animal applications.

Terms such as "left", "right", "up", "down", "bottom", "top", "front", "back", "in", "out" and the like are applicable in conjunction with the drawings. These terms are merely for the purposes of description and do not necessarily apply to the position in which the tampon may be constructed or used.

While a particular embodiment of the tampon and pleated cover has been shown and described it is to be understood the invention is not limited thereto and protection is sought to the broadest extent the prior art allows.

What is claimed is:

1. A tampon assembly adapted for use in and with a body opening, said tampon assembly including:

(a) a helically-wound absorbent member providing a body portion with said absorbent member being close-wound with the side portions thereof substantially parallel and in an assembled condition providing a substantially continuous and contiguous outer surface, said member having sufficient memory to withstand insertion manipulation;

(b) a withdrawal string attached at one end to that end on the helically-wound absorbent member that is disposed to face said body opening;

(c) a permeable cover having a closed end contoured and prepared for entry into said body opening, said cover disposed adjacent to the absorbent member and enclosing and retaining said withdrawal string, the cover having a plurality of pleated or accordion folds providing overlays arranged so that in an inserting condition the pleats or folds in the cover are disposed to remain in their overlaid condition and remain so during use, and with this cover closed sufficiently at a second end so as to snugly capture the withdrawal string to prevent unwanted exiting of the absorbent material through said closure, and (d) means for inserting the tampon into a body opening and when the tampon is to be withdrawn from said body opening the withdrawal string is grasped and pulled to commence withdrawal of the tampon whereat the helically-wound absorption member is sufficiently uncoiled to at least partially collapse said member into a smaller diameter with the attached string also engaging and withdrawing the pleated cover in which the pleats unfold as the overlaid cover is moved outwardly to bring said cover into a substantially straightened condition and causing the coiled absorbent material to be at least partially straightened out thus removal from the body opening is comfortably achieved due to a reduction of diameter of the tampon.

2. A tampon as in claim 1 in which the absorbent material is made as an extrusion with the cross section thereof substantially the finished size.

3. A tampon as in claim 2 in which the cross section is substantially a square.

4. A tampon as in claim 2 in which the cross section is substantially a rectangle.

5. A tampon as in claim 2 in which the cross section has a configuration with a generally flat top and with adjacent sides generally normal to the plane of the top, said sides also substantially parallel to each other.

6. A tampon as in claim 1 in which a lubricant is applied to the outer surface of the cover member to assist in the insertion.

7. A tampon as in claim 1 in which the absorbent member is regular in cross section for its full length and the attachment of the withdrawal string is to a portion of the last coil of the helical winding.

* * * * *